(12) United States Patent
Meguro

(10) Patent No.: US 11,957,483 B2
(45) Date of Patent: Apr. 16, 2024

(54) IMAGE PROCESSING DEVICE AND METHOD OF OPERATING THE SAME

(71) Applicant: FUJIFILM Corporation, Tokyo (JP)

(72) Inventor: Misaki Meguro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 328 days.

(21) Appl. No.: 17/506,932

(22) Filed: Oct. 21, 2021

(65) Prior Publication Data

US 2022/0039743 A1 Feb. 10, 2022

Related U.S. Application Data

(63) Continuation of application No. PCT/JP2020/014840, filed on Mar. 31, 2020.

(30) Foreign Application Priority Data

Apr. 23, 2019 (JP) ................. 2019-082245

(51) Int. Cl.
*A61B 1/00* (2006.01)
*A61B 5/00* (2006.01)
*A61B 5/02* (2006.01)
*G06T 7/246* (2017.01)
*G06V 10/56* (2022.01)
*G06V 10/60* (2022.01)

(52) U.S. Cl.
CPC .......... *A61B 5/4842* (2013.01); *A61B 5/0071* (2013.01); *A61B 5/02042* (2013.01); *A61B 5/4216* (2013.01); *A61B 5/4255* (2013.01); *G06V 10/56* (2022.01); *G06V 10/60* (2022.01); *G06V 2201/031* (2022.01)

(58) Field of Classification Search
USPC ................ D24/107, 164–170; 128/915–925; 382/128–134, 154–224; 600/300–349, 600/408, 431–530, 101–183, 248–249; 604/19–20; 706/1–62, 900–903
See application file for complete search history.

(56) References Cited

U.S. PATENT DOCUMENTS

2014/0031628 A1 1/2014 Kaku
2017/0112355 A1 4/2017 Hirota et al.
(Continued)

FOREIGN PATENT DOCUMENTS

JP 2014-023591 A 2/2014
JP 2016-016185 A 2/2016
(Continued)

OTHER PUBLICATIONS

Aoyama Tatsuya;Processor Device and Endoscopic System; May 3, 2018 (Year: 2018).*
(Continued)

*Primary Examiner* — Marcellus J Augustin
(74) *Attorney, Agent, or Firm* — Studebaker & Brackett PC

(57) ABSTRACT

A disease-related processing section performs at least one of the calculation of an index value related to a stage of ulcerative colitis, the determination of the stage of the ulcerative colitis, or the determination of whether or not the ulcerative colitis has remitted, on the basis of the denseness of superficial blood vessels, intramucosal hemorrhage, and extramucosal hemorrhage obtained from a medical image.

11 Claims, 15 Drawing Sheets

(56) References Cited

U.S. PATENT DOCUMENTS

| | | | |
|---|---|---|---|
| 2019/0059707 A1 | 2/2019 | Watanabe | |
| 2019/0073769 A1* | 3/2019 | Watanabe | A61B 5/1459 |
| 2019/0239737 A1 | 8/2019 | Aoyama | |
| 2022/0114730 A1* | 4/2022 | Duval | G16H 10/60 |

FOREIGN PATENT DOCUMENTS

| | | |
|---|---|---|
| JP | 2019-037688 A | 3/2019 |
| JP | 2019-042157 A | 3/2019 |
| RU | 2427322 C1 | 8/2011 |
| RU | 2601116 C1 | 10/2016 |
| WO | 2018/079217 A1 | 5/2018 |

OTHER PUBLICATIONS

Simon P L Travis; Developing an instrument to assess the endoscopic severity of ulcerative colitis: the Ulcerative Colitis Endoscope Index of Severity (UCEIS); Oct. 13, 2011 (Year: 2011).*

Watanabe Hiroki; Medical Image Processing Apparatus, Endoscope Apparatus, Diagnostic Support Apparatus, and Medical Service Support Apparatus; 2019 (Year: 2019).*

Medical Image Processing Apparatus, Endoscope Apparatus, Diagnostic Support Apparatus, and Medical Service Support Apparatus (Year: 2019).*

An Office Action; "Notice of Reasons for Refusal", mailed by the Japanese Patent Office dated May 6, 2022, which corresponds to Japanese Patent Application No. 2021-515923 and is related to U.S. Appl. No. 17/506,932 with English language translation.

Travis Simon P. L. et al., "Developing an instrument to assess the endoscopic severity of ulcerative colitis: the Ulcerative Colitis Endoscopic Index of Severity (UCEIS)", Gut Microbiota; vol. 61, No. 4; Apr. 1, 2012; pp. 535-542; XP055918444; doi:10.1136/gutjnl-2011-300486.

Bossuyt P. et al.; "Automated real-time endoscopic scoring based on machine learning in ulcerative colitis: Red Density reliability and responsiveness study", Abstracts of the 14th Congress of ECCO—European Crohn's and Colitis Organisation; Jan. 25, 2019; pp. 187-188; XP055918265.

The partial supplementary European search report (R. 164 EPC) issued by the European Patent Office dated May 16, 2022, which corresponds to European Application No. 20795229.2-1210 and is related to U.S. Appl. No. 17/506,932.

An Office Action mailed by China National Intellectual Property Administration dated Jul. 22, 2023, which corresponds to Chinese Application No. 202080030966.3 and is related to U.S. Appl. No. 17/506,932; with English language translation.

International Search Report issued in PCT/JP2020/014840; dated Jun. 16, 2020.

International Preliminary Report on Patentability and Written Opinion issued in PCT/JP2020/014840; dated Sep. 28, 2021.

Hideki Ishikawa et al, Problems related to judgment of cure of ulcerative colitis, Gastroenterological Endoscopy, Jan. 20, 1990, vol. 32, No. 1, pp. 262-263.

The extended European search report issued by the European Patent Office dated Aug. 17, 2022, which corresponds to European Application No. 20795229.2-1210 and is related to U.S. Appl. No. 17/506,932.

An Office Action mailed by China National Intellectual Property Administration on Jan. 17, 2024, which corresponds to Chinese Patent Application No. 202080030966.3 and is related to U.S. Appl. No. 17/506,932 with English language translation.

* cited by examiner

IMAGE PROCESSING DEVICE AND METHOD OF OPERATING THE SAME

CROSS-REFERENCE TO RELATED APPLICATIONS

This application is a Continuation of PCT International Application No. PCT/JP2020/014840 filed on 31 Mar. 2020, which claims priority under 35 U.S.C § 119(a) to Japanese Patent Application No. 2019-082245 filed on 23 Apr. 2019. The above application is hereby expressly incorporated by reference, in its entirety, into the present application.

BACKGROUND OF THE INVENTION

1. Field of the Invention

The present invention relates to an image processing device that performs processing related to a disease and a method of operating the image processing device.

2. Description of the Related Art

In a medical field, a diagnosis is widely made using a medical image. For example, there is an endoscope system that comprises a light source device, an endoscope, and a processor device as an apparatus using a medical image. In the endoscope system, an object to be observed is irradiated with illumination light and an endoscopic image as a medical image is acquired from the image pickup of the object to be observed illuminated with the illumination light. The endoscopic image is displayed on a monitor and is used for diagnosis.

In recent years, processing has been performed on the basis of an endoscopic image, so that information for supporting a diagnosis, such as the determination of an abnormal region, such as a lesion area, has also been provided to a user. In, for example, JP2016-16185A (corresponding to US2017/112355A1), a sharpness-reduction region that is a region of a mucosal region in which the sharpness of blood vessels of a visible vascular pattern is reduced is extracted as a candidate region of an abnormal region in which a visible vascular pattern has locally disappeared and whether or not the candidate region is an abnormal region is then determined on the basis of the shape of the candidate region of the abnormal region.

SUMMARY OF THE INVENTION

Ulcerative colitis (UC) is known as one of the diseases of the large intestine. The determination of whether or not ulcerative colitis has remitted is currently made by a biopsy performed after endoscopic diagnosis. Accordingly, it has been required to determine whether or not ulcerative colitis has remitted without performing a biopsy.

An object of the invention is to provide an image processing device that can perform at least one of the calculation of an index value related to a stage of ulcerative colitis, the determination of a stage of ulcerative colitis, or the determination of whether or not ulcerative colitis has remitted without performing a biopsy, and a method of operating the image processing device.

An image processing device according to an aspect of the invention comprises a processor that acquires a medical image obtained from image pickup of an object to be observed and performs at least one of calculation of an index value related to a stage of ulcerative colitis, determination of the stage of the ulcerative colitis, or determination of whether or not the ulcerative colitis has remitted, on the basis of denseness of superficial blood vessels, intramucosal hemorrhage, and extramucosal hemorrhage obtained from the medical image.

It is preferable that, in a case where the processor determines whether or not the ulcerative colitis has remitted, the processor classifies the denseness of the superficial blood vessels, the intramucosal hemorrhage, and the extramucosal hemorrhage depending on a frequency characteristic or a luminance value obtained from the medical image and determines whether or not the ulcerative colitis has remitted according to the classification.

It is preferable that, in a case where the processor determines whether or not the ulcerative colitis has remitted, the processor calculates a frequency component-space distribution from the medical image, extracts a first frequency characteristic region having a first frequency characteristic, extracts a second frequency characteristic region having a second frequency characteristic having a frequency higher than a frequency of the first frequency characteristic, and extracts a third frequency characteristic region having a third frequency characteristic having a frequency higher than the frequency of the second frequency characteristic on the basis of the frequency component-space distribution, detects the denseness of the superficial blood vessels, the intramucosal hemorrhage, and the extramucosal hemorrhage on the basis of the first frequency characteristic region that is subjected to first region determination processing using a luminance value, the second frequency characteristic region that is subjected to second region determination processing using a luminance value, and the third frequency characteristic region, and determines whether or not the ulcerative colitis has remitted on the basis of the detected denseness of the superficial blood vessels, the detected intramucosal hemorrhage, and the detected extramucosal hemorrhage.

It is preferable that the processor extracts the first frequency characteristic region on the basis of the frequency component-space distribution, extracts the third frequency characteristic region on the basis of the frequency component-space distribution, detects an analysis target region excluding the first frequency characteristic region from the medical image, and extracts the second frequency characteristic region by excluding the third frequency characteristic region from the analysis target region.

It is preferable that the processor detects the extramucosal hemorrhage by performing the first region determination processing on the first frequency characteristic region, detects the intramucosal hemorrhage by performing the second region determination processing on the second frequency characteristic region, and detects the third frequency characteristic region as the denseness of the superficial blood vessels.

It is preferable that the processor determines that the ulcerative colitis has not remitted in a case where any of a condition where the superficial blood vessels are dense, a condition where an amount of the detected intramucosal hemorrhage is equal to or larger than a threshold value for intramucosal hemorrhage, a condition where an amount of the detected extramucosal hemorrhage is equal to or larger than a threshold value for extramucosal hemorrhage, or a condition where a sum of the amount of the detected intramucosal hemorrhage and the amount of the detected extramucosal hemorrhage is equal to or larger than a threshold value for intramucosal/extramucosal hemorrhage is satisfied, and the processor determines that the ulcerative colitis has remitted in a case where all of the condition where the superficial blood vessels are dense, the condition where the amount of the detected intramucosal hemorrhage is equal to or larger than the threshold value for intramucosal hemorrhage, the condition where the amount of the detected extramucosal hemorrhage is equal to or larger than the threshold value for extramucosal hemorrhage, and the condition where the sum of the amount of the detected intramucosal hemorrhage and the amount of the detected extramucosal hemorrhage is equal to or larger than the threshold value for intramucosal/extramucosal hemorrhage are not satisfied.

It is preferable that the medical image is obtained from the image pickup of the object to be observed that is illuminated with illumination light including short-wavelength light. It is preferable that the illumination light is violet light of which a central wavelength or a peak wavelength includes 410 nm. It is preferable that the illumination light is narrow-band blue light and narrow-band green light as the short-wavelength light and the medical image is obtained from the image pickup of the object to be observed that is alternately illuminated with the narrow-band blue light and the narrow-band green light. It is preferable that the illumination light is pseudo-white light including the short-wavelength light and fluorescence that is obtained in a case where a phosphor is irradiated with excitation light. It is preferable that the illumination light includes violet light as the short-wavelength light and blue light, green light, or red light.

In a method of operating an image processing device according to another aspect of the invention, the image processing device includes a processor and the processor includes an image acquisition step of acquiring a medical image obtained from image pickup of an object to be observed, and a determination step of performing at least one of calculation of an index value related to a stage of ulcerative colitis, determination of the stage of the ulcerative colitis, or determination of whether or not the ulcerative colitis has remitted, on the basis of denseness of superficial blood vessels, intramucosal hemorrhage, and extramucosal hemorrhage obtained from the medical image.

It is preferable that, in a case where the processor determines whether or not the ulcerative colitis has remitted in the determination step, in the determination step, the processor includes a step of calculating a frequency component-space distribution from the medical image, a step of extracting a first frequency characteristic region having a first frequency characteristic, extracting a second frequency characteristic region having a second frequency characteristic having a frequency higher than a frequency of the first frequency characteristic, and extracting a third frequency characteristic region having a third frequency characteristic having a frequency higher than the frequency of the second frequency characteristic on the basis of the frequency component-space distribution, a step of detecting the denseness of the superficial blood vessels, the intramucosal hemorrhage, and the extramucosal hemorrhage on the basis of the first frequency characteristic region that is subjected to first region determination processing using a luminance value, the second frequency characteristic region that is subjected to second region determination processing using a luminance value, and the third frequency characteristic region, and a step of determining whether or not the ulcerative colitis has remitted on the basis of the detected denseness of the superficial blood vessels, the detected intramucosal hemorrhage, and the detected extramucosal hemorrhage.

According to the invention, it is possible to perform at least one of the calculation of an index value related to a stage of ulcerative colitis, the determination of a stage of ulcerative colitis, or the determination of whether or not ulcerative colitis has remitted.

DESCRIPTION OF THE PREFERRED EMBODIMENTS

First Embodiment

Figure 1:
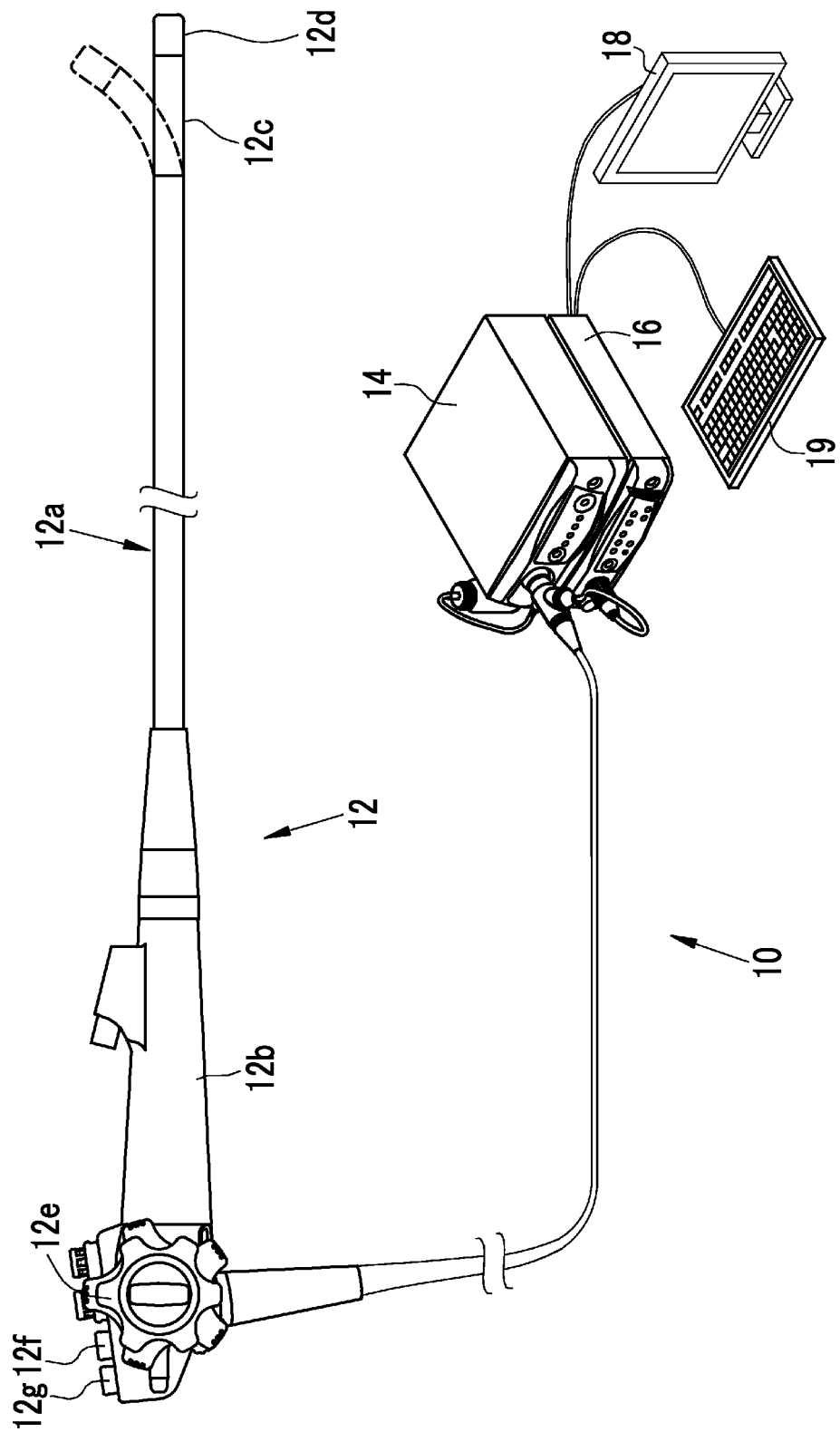
FIG. 1 is a diagram showing the appearance of an endoscope system.

As shown in FIG. 1, an endoscope system 10 includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12a that is to be inserted into the body of an object to be observed, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d is made to face in a desired direction.

Further, the operation part 12b is provided with a mode changeover switch (SW) 12f that is used for an operation for switching a mode and a static image-acquisition instruction unit 12g that is used for an instruction to acquire the static image of the object to be observed, in addition to the angle knobs 12e.

The endoscope system 10 has three modes, that is, a normal light mode, a special light mode, and a disease-related processing mode. In the normal light mode, the object to be observed is illuminated with normal light and the image of the object to be observed is picked up, so that a normal image having a natural hue is displayed on the monitor 18. In the special light mode, the object to be observed is illuminated with special light having a wavelength range different from the wavelength range of normal light and the image of the object to be observed is picked up, so that a special light image in which a specific structure is enhanced is displayed on the monitor 18. In the disease-related processing mode, whether or not ulcerative colitis, which is one of diseases, has remitted is determined on the basis of the normal image or the special image. In the disease-related processing mode, an index value related to the stage of ulcerative colitis may be calculated or the stage of ulcerative colitis may be determined.

The special image (endoscopic image) is used in the disease-related processing mode in this embodiment, but the normal image may be used. Further, medical images, such as a radiographic image obtained from a radiographic device, a CT image obtained from computed tomography (CT), and a MRI image obtained from magnetic resonance imaging (MRI), may be used as an image, which is used in the disease-related processing mode, in addition to the special image as an endoscopic image that is one of medical images. Furthermore, the disease-related processing mode is performed in the processor device 16 to which the endoscope 12 is connected, but may be performed by other methods. For example, an external image processing device separate from the endoscope system 10 may be provided with the function of a disease-related processing section 66, a medical image may be input to the external image processing device to perform the disease-related processing mode, and the result of the disease-related processing mode may be displayed on an external monitor connected to the external image processing device.

The processor device 16 is electrically connected to the monitor 18 and the console 19. The monitor 18 outputs and displays the image of the object to be observed, information incidental to the image of the object to be observed, and the like. The console 19 functions as a user interface that receives an input operation, such as function settings. An external recording unit (not shown), which records images, image information, and the like, may be connected to the processor device 16. Further, the processor device 16 corresponds to an image processing device according to an embodiment of the invention.

Figure 2:
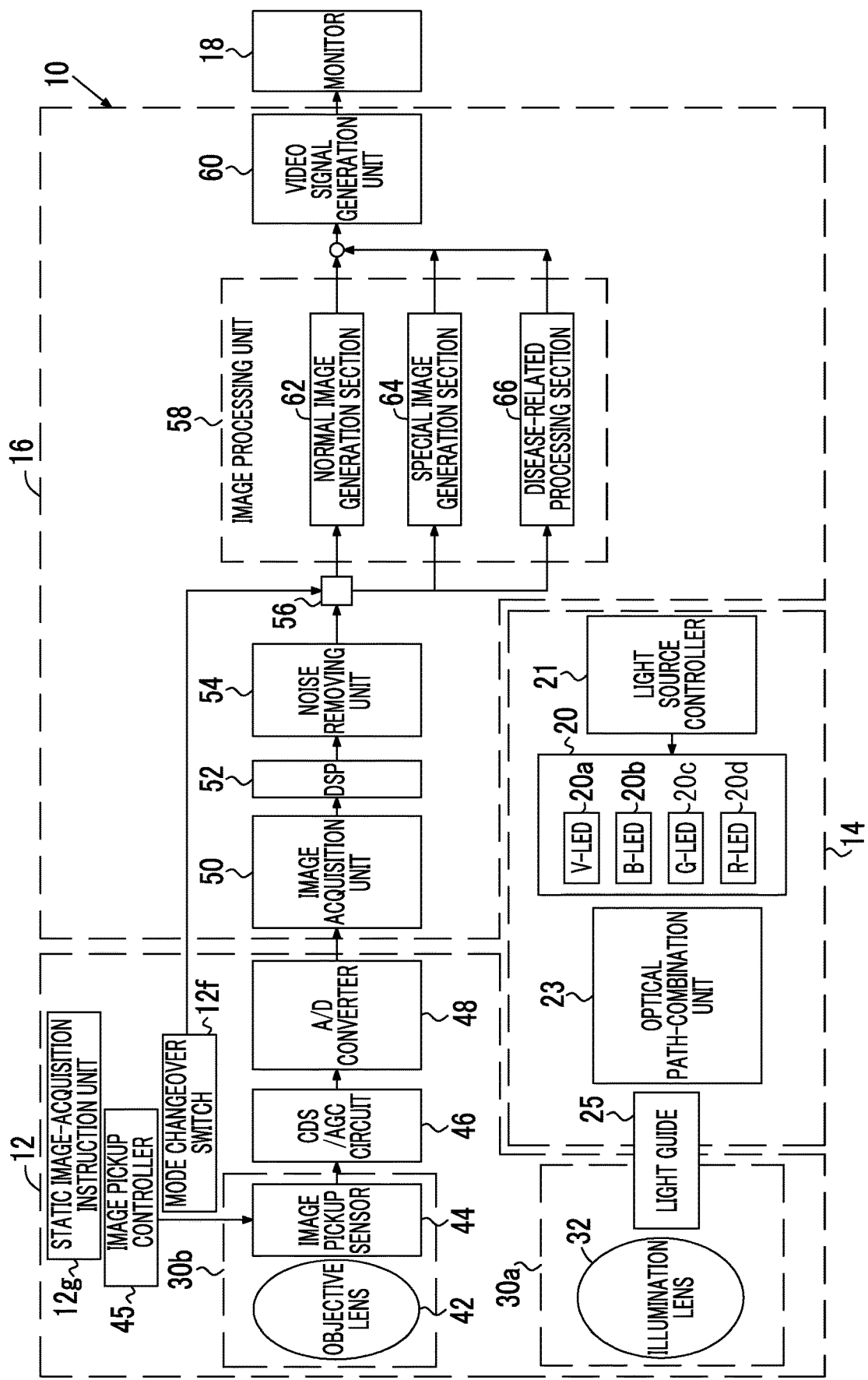
FIG. 2 is a block diagram showing the functions of the endoscope system of a first embodiment.

In FIG. 2, the light source device 14 comprises a light source unit 20 and a light source controller 21 that controls the light source unit 20. The light source unit 20 includes, for example, a plurality of semiconductor light sources, turns on or off each of these semiconductor light sources, and emits illumination light, which illuminates the object to be observed, by controlling the amount of emitted light in a case where each semiconductor light source is turned on. In this embodiment, the light source unit 20 includes four color LEDs, that is, a violet light emitting diode (V-LED) 20a, a blue light emitting diode (B-LED) 20b, a green light emitting diode (G-LED) 20c, and a red light emitting diode (R-LED) 20d.

Figure 3:
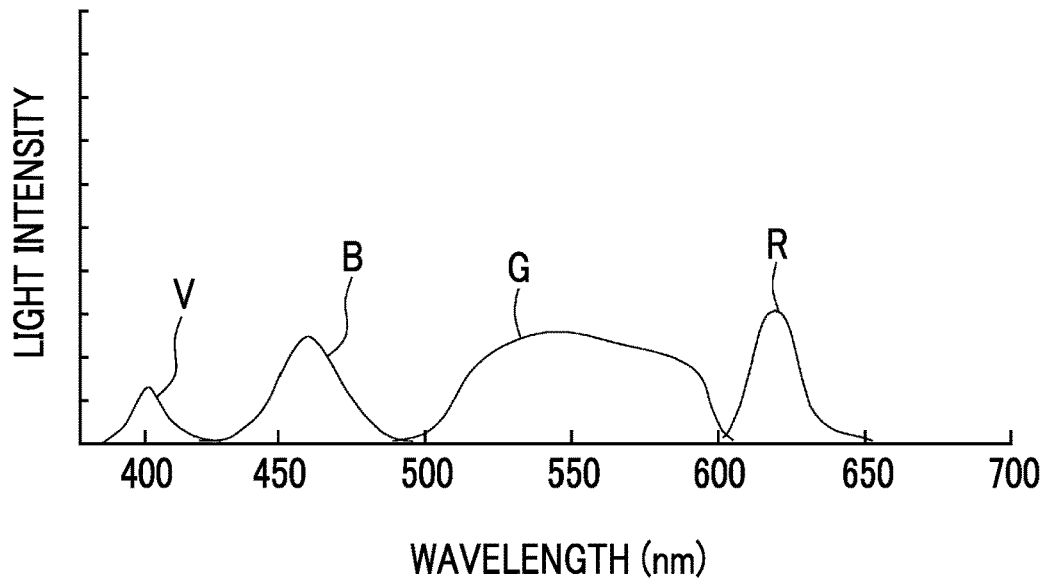
FIG. 3 is a graph showing the spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm. Violet light V is short-wavelength light that is used to detect the denseness of superficial blood vessels, intramucosal hemorrhage, and extramucosal hemorrhage used in the disease-related processing mode, and it is preferable that violet light V has a central wavelength or a peak wavelength including 410 nm.

The light source controller 21 controls the V-LED 20a, the B-LED 20b, the G-LED 20c, and the R-LED 20d. Further, the light source controller 21 controls the respective LEDs 20a to 20d so that normal light of which the light intensity ratios of violet light V, blue light B, green light G, and red light R are Vc:Bc:Gc:Rc is emitted in the normal light mode.

Figure 4:
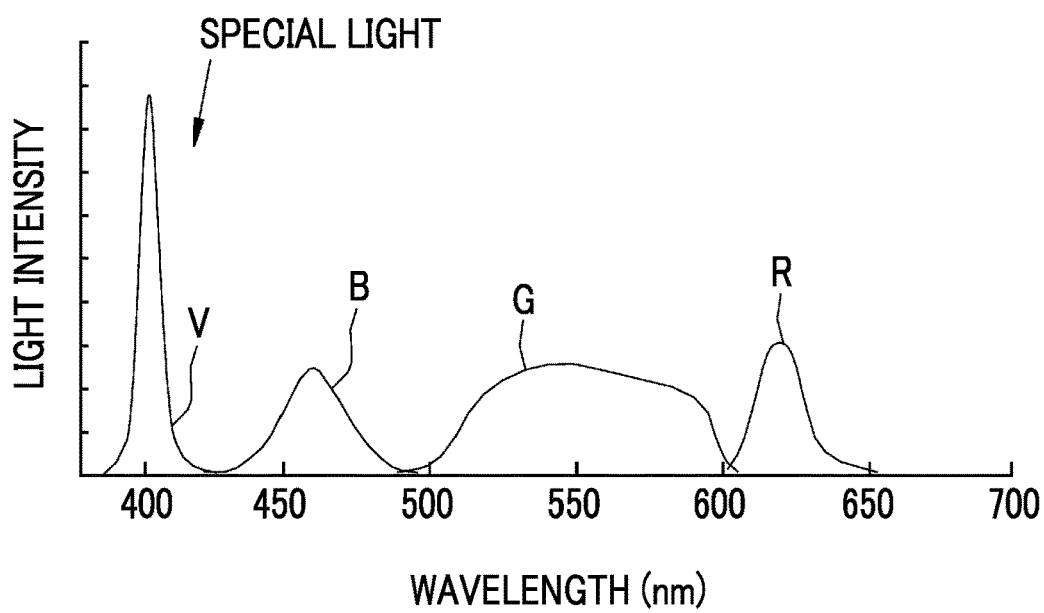
FIG. 4 is a graph showing the spectrum of special light of the first embodiment.
Figure 5:
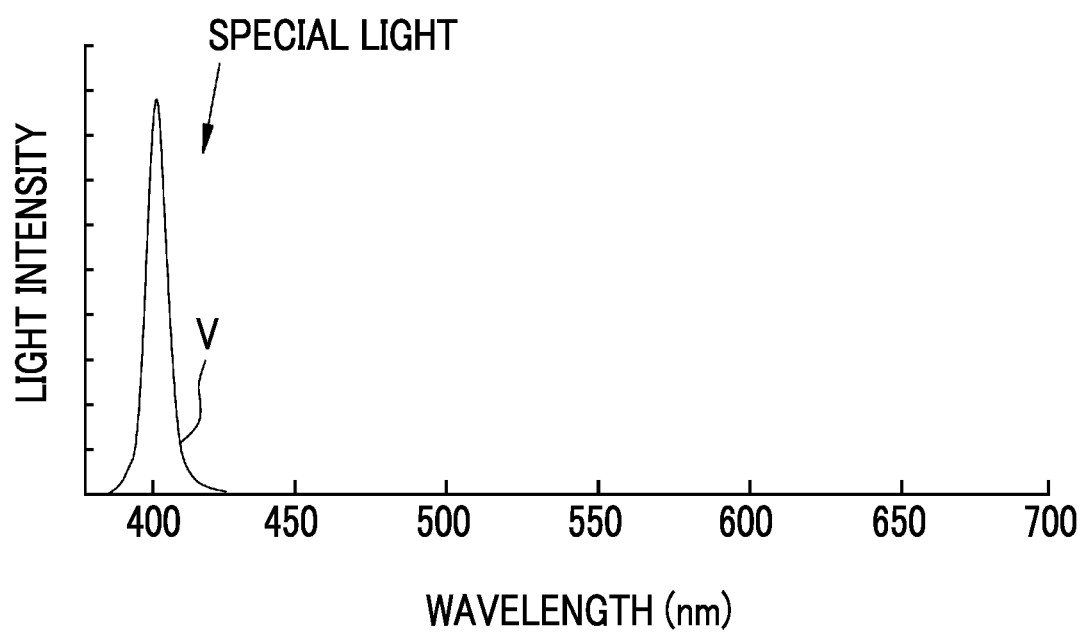
FIG. 5 is a graph showing the spectrum of special light that includes only violet light V.

Furthermore, the light source controller 21 controls the respective LEDs 20a to 20d so that special light of which the light intensity ratios of violet light V as short-wavelength light, blue light B, green light G, and red light R are Vs:Bs:Gs:Rs is emitted in the special light mode or the disease-related processing mode. It is preferable that special light having the light intensity ratios Vs:Bs:Gs:Rs emphasizes superficial blood vessels and the like. For this purpose, it is preferable that the light intensity of violet light V of first illumination light is set to be higher than the light intensity of blue light B thereof. For example, as shown in FIG. 4, a ratio of the light intensity Vs of violet light V to the light intensity Bs of blue light B is set to "4:1". Further, as shown in FIG. 5, with regard to special light, the light intensity ratios of violet light V, blue light B, green light G, and red light R are set to 1:0:0:0 and only violet light V as short-wavelength light may be emitted.

In this specification, the light intensity ratios include a case where the ratio of at least one semiconductor light source is 0 (zero). Accordingly, the light intensity ratios include a case where any one or two or more of the respective semiconductor light sources are not turned on. For example, even though only one semiconductor light source is turned on and the other three semiconductor light sources are not turned on as in a case where the light intensity ratios of violet light V, blue light B, green light G, and red light R are 1:0:0:0, it is regarded that the light source unit 20 has light intensity ratios.

Light emitted from each of the LEDs 20a to 20d is incident on a light guide 25 through an optical path-combination unit 23 that is composed of a mirror, a lens, and the like. The light guide 25 is built in the endoscope 12 and a universal cord (a cord connecting the endoscope 12 to the light source device 14 and the processor device 16). The light guide 25 transmits light, which is emitted from the optical path-combination unit 23, to the distal end part 12d of the endoscope 12.

The distal end part 12d of the endoscope 12 is provided with an illumination optical system 30a and an image pickup optical system 30b. The illumination optical system 30a includes an illumination lens 32, and the object to be observed is irradiated with illumination light, which is transmitted by the light guide 25, through the illumination lens 32. The image pickup optical system 30b includes an objective lens 42 and an image pickup sensor 44. Light, which is emitted from the object to be observed since the object to be observed is irradiated with illumination light, is incident on the image pickup sensor 44 through the objective lens 42. Accordingly, the image of the object to be observed is formed on the image pickup sensor 44.

A charge coupled device (CCD) image pickup sensor or a complementary metal-oxide semiconductor (CMOS) image pickup sensor can be used as the image pickup sensor 44. Further, a complementary color image pickup sensor, which comprises complementary color filters corresponding to C (cyan), M (magenta), Y (yellow), and G (green), may be used instead of the primary color image pickup sensor 44. In a case where a complementary color image pickup sensor is used, image signals corresponding to four colors of C, M, Y, and G are output. Accordingly, the image signals corresponding to four colors of C, M, Y, and G are converted into image signals corresponding to three colors of R, G, and B by complementary color-primary color conversion, so that image signals corresponding to the same respective colors of R, G, and B as those of the image pickup sensor 44 can be obtained.

The image pickup sensor 44 is driven and controlled by the image pickup controller 45. Control performed by the image pickup controller 45 varies depending on the respective modes. In the normal light mode, the image pickup controller 45 controls the image pickup sensor 44 so that the image pickup sensor 44 picks up the image of the object to be observed illuminated with normal light. Accordingly, Bc-image signals are output from B-pixels of the image pickup sensor 44, Gc-image signals are output from G-pixels thereof, and Rc-image signals are output from R-pixels thereof.

In the special light mode, the image pickup controller 45 controls the image pickup sensor 44 to pick up the image of the object to be observed illuminated with special light. Accordingly, Bs-image signals are output from the B-pixels of the image pickup sensor 44, Gs-image signals are output from the G-pixels thereof, and Rs-image signals are output from the R-pixels thereof.

A correlated double sampling/automatic gain control (CDS/AGC) circuit 46 performs correlated double sampling (CDS) or automatic gain control (AGC) on the analog image signal that are obtained from the image pickup sensor 44. The image signals, which have been transmitted through the CDS/AGC circuit 46, are converted into digital image signals by an analog/digital (A/D) converter 48. The digital image signals, which have been subjected to A/D conversion, are input to the processor device 16.

The processor device 16 comprises an image acquisition unit 50, a digital signal processor (DSP) 52, a noise removing unit 54, an image processing switching unit 56, an image processing unit 58, and a video signal generation unit 60. The image processing unit 58 comprises a normal image generation section 62, a special image generation section 64, and a disease-related processing section 66.

In the processor device 16, programs related to various types of processing, such as the calculation of the index value, the determination of the stage, and the determination of whether or not ulcerative colitis has remitted, are incorporated in a program memory (not shown). The programs incorporated in the program memory are operated by a central controller (not shown) formed of a processor, so that the functions of the image acquisition unit 50, the DSP 52, the noise removing unit 54, the image processing switching unit 56, the image processing unit 58, and the video signal generation unit 60 are realized. Accordingly, the functions of the normal image generation section 62, the special image generation section 64, and the disease-related processing section 66 are realized. The disease-related processing section 66 realizes the functions of a frequency component space distribution-calculation section 70, a frequency characteristic region-extraction section 72, a structure detection section 74, and a determination section 76 (see FIG. 9).

The image acquisition unit 50 acquires the image signals of an endoscopic image that is one of medical images input from the endoscope 12. The acquired image signals are transmitted to the DSP 52. The DSP 52 performs various types of signal processing, such as defect correction processing, offset processing, gain correction processing, linear matrix processing, gamma conversion processing, demosaicing processing, and YC conversion processing, on the received image signals. Signals of defective pixels of the image pickup sensor 44 are corrected in the defect correction processing. Dark current components are removed from the image signals having been subjected to the defect correction processing in the offset processing, so that an accurate zero level is set. The image signals, which have been subjected to the offset processing and correspond to each color, are multiplied by a specific gain in the gain correction processing, so that the signal level of each image signal is adjusted. The linear matrix processing for improving color reproducibility is performed on the image signals that have been subjected to the gain correction processing and correspond to each color.

After that, the brightness or chroma saturation of each image signal is adjusted by the gamma conversion processing. The demosaicing processing (also referred to as equalization processing or demosaicing) is performed on the image signals having been subjected to the linear matrix processing, so that signals corresponding to colors missed in the respective pixels are generated by interpolation. All the pixels are made to have signals corresponding to the respective colors of R, G, and B by the demosaicing processing. The DSP 52 performs the YC conversion processing on the respective image signals having been subjected to the demosaicing processing, and outputs luminance signals Y, color difference signals Cb, and color difference signals Cr to the noise removing unit 54.

The noise removing unit 54 performs noise removal processing, which is performed using, for example, a moving-average method, median filtering, or the like, on the image signals that have been subjected to the demosaicing processing and the like by the DSP 52. The image signals from which noise has been removed are input to the image processing switching unit 56.

The image processing switching unit 56 switches a destination, to which the image signals output from the noise removing unit 54 are transmitted, to any of the normal image generation section 62, the special image generation section 64, or the disease-related processing section 66. Specifically, in a case where the endoscope system 10 is set to the normal light mode, the image signals output from the noise removing unit 54 are input to the normal image generation section 62. In a case where the endoscope system 10 is set to the special light mode, the image signals output from the noise removing unit 54 are input to the special image generation section 64. In a case where the endoscope system 10 is set to the disease-related processing mode, the image signals output from the noise removing unit 54 are input to the disease-related processing section 66.

The normal image generation section 62 performs image processing for a normal image on Rc-image signals, Gc-image signals, and Bc-image signals that are input and correspond to one frame. The image processing for a normal image includes color conversion processing, such as 3×3-matrix processing, gradation transformation processing, and three-dimensional look up table (LUT) processing, and structure enhancement processing, such as color enhancement processing and spatial frequency emphasis. The Rc-image signals, the Gc-image signals, and the Bc-image signals having been subjected to the image processing for a normal image are input to the video signal generation unit 60 as a normal image.

The special image generation section 64 performs image processing for a special image on Rs-image signals, Gs-image signals, and Bs-image signals that are input and correspond to one frame. The image processing for a special image includes color conversion processing, such as 3×3-matrix processing, gradation transformation processing, and three-dimensional look up table (LUT) processing, and structure enhancement processing, such as color enhancement processing and spatial frequency emphasis. The Rs-image signals, the Gs-image signals, and the Bs-image signal having been subjected to the image processing for a special image are input to the video signal generation unit 60 as a special image.

The disease-related processing section 66 performs at least one of the calculation of the index value related to the stage of ulcerative colitis, the determination of the stage of ulcerative colitis, or the determination of whether or not ulcerative colitis has remitted, on the basis of the denseness of superficial blood vessels, intramucosal hemorrhage, and extramucosal hemorrhage that are obtained from the special image. Information about a determination result is input to the video signal generation unit 60. The details of the disease-related processing section 66 will be described later. A case where the disease-related processing section 66 determines whether or not ulcerative colitis has remitted will be described in the first to third embodiments.

The video signal generation unit 60 converts the normal image, the special image, or the information about the determination result, which is output from the image processing unit 58, into video signals that can be displayed in full color on the monitor 18. The video signals having been converted are input to the monitor 18. Accordingly, the normal image, the special image, or the information about the determination result is displayed on the monitor 18.

Figures 6A, 6B, 6C, 6D, 6E:
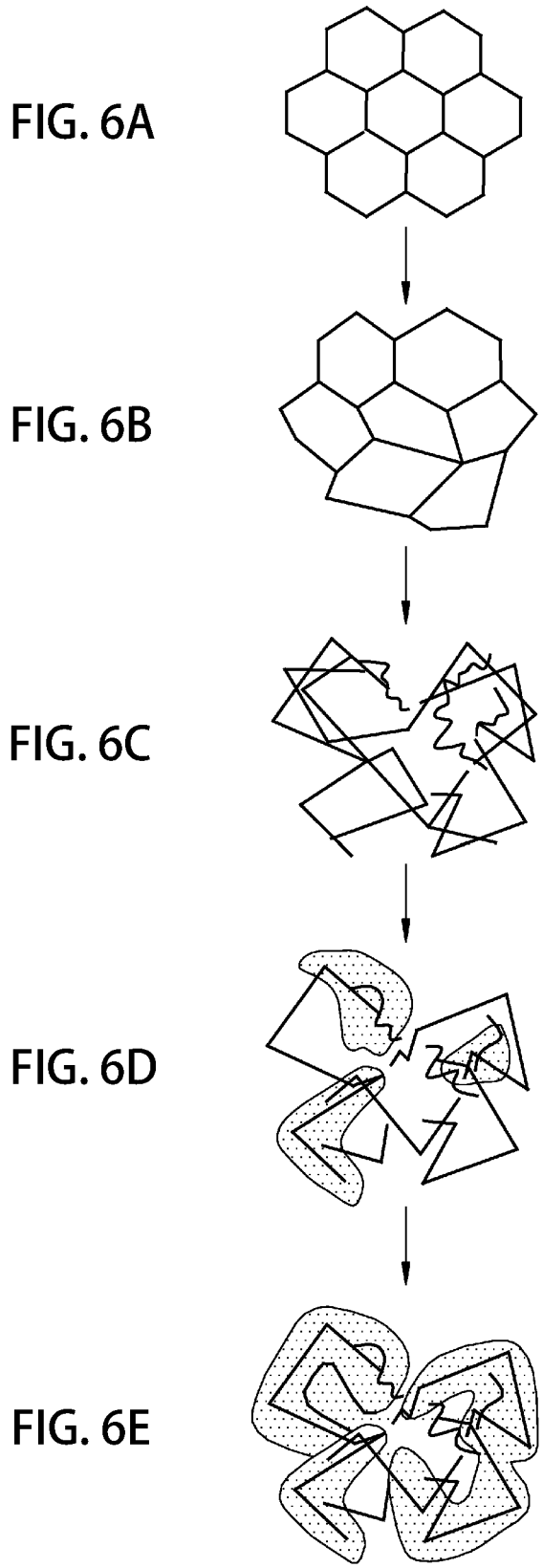
FIGS. 6A to 6E are diagrams illustrating the pattern of the vascular structure that is changed depending on the severity of ulcerative colitis.

The details of the disease-related processing section 66 will be described below. The inventors find out that the pattern of a vascular structure changes as shown in FIGS. 6A to 6E whenever the severity of ulcerative colitis, which is an object to be determined by the disease-related processing section 66, worsens. In a case where ulcerative colitis has remitted or ulcerative colitis has not occurred, the pattern of superficial blood vessels is regular (FIG. 6A) or the regularity of the pattern of the superficial blood vessels is broken somewhat (FIG. 6B). On the other hands, in a case where ulcerative colitis has not remitted and the severity of ulcerative colitis is mild, the superficial blood vessels are dense (FIG. 6C). Further, in a case where ulcerative colitis has not remitted and the severity of ulcerative colitis is moderate, intramucosal hemorrhage occurs (FIG. 6D). Furthermore, in a case where ulcerative colitis has not remitted and the severity of ulcerative colitis is moderate to severe, extramucosal hemorrhage occurs (FIG. 6E). The disease-related processing section 66 uses a change in the pattern of the vascular structure to determine whether or not ulcerative colitis has remitted on the basis of the special image that is one of medical images.

Figure 7:
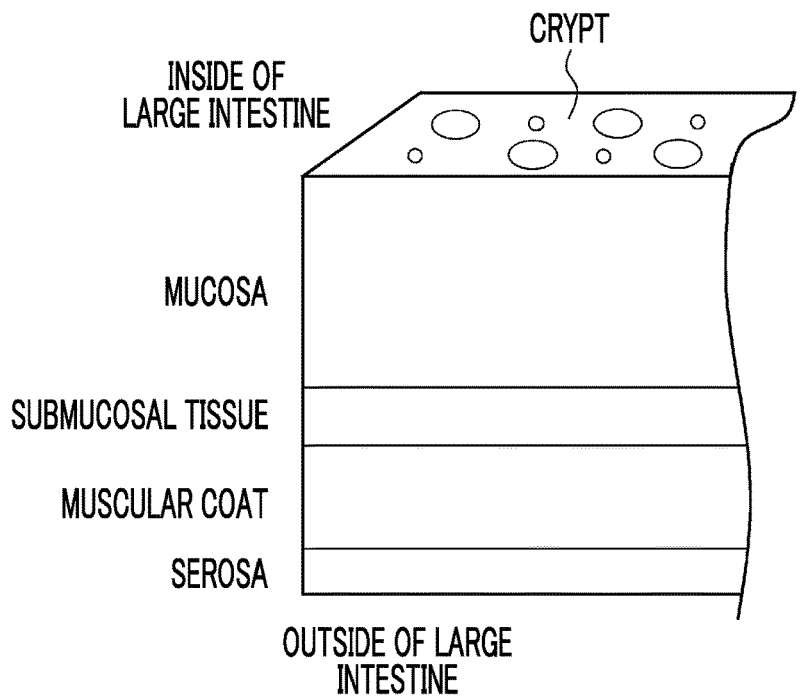
FIG. 7 is a cross-sectional view showing the cross section of the large intestine.

Here, "the denseness of superficial blood vessels" means a state where superficial blood vessels meander and are gathered, and means that many superficial blood vessels surround the crypt (see FIG. 7) in terms of appearance on an image. "Intramucosal hemorrhage" means bleeding in the mucosal tissue (see FIG. 7) and requires to be discriminated from bleeding into an inner cavity. "Intramucosal hemorrhage" means bleeding that is not in a mucosa and an inner cavity (the lumen and a hole having plicae) in terms of appearance on an image. "Extramucosal hemorrhage" means a small amount of blood that flows into the lumen, blood that is oozed from the lumen or the mucosa positioned in front of the endoscope even after the washing of the inside of the lumen and can be visually recognized, or blood in the lumen that is caused by bleeding on a hemorrhagic mucosa.

Figure 8:
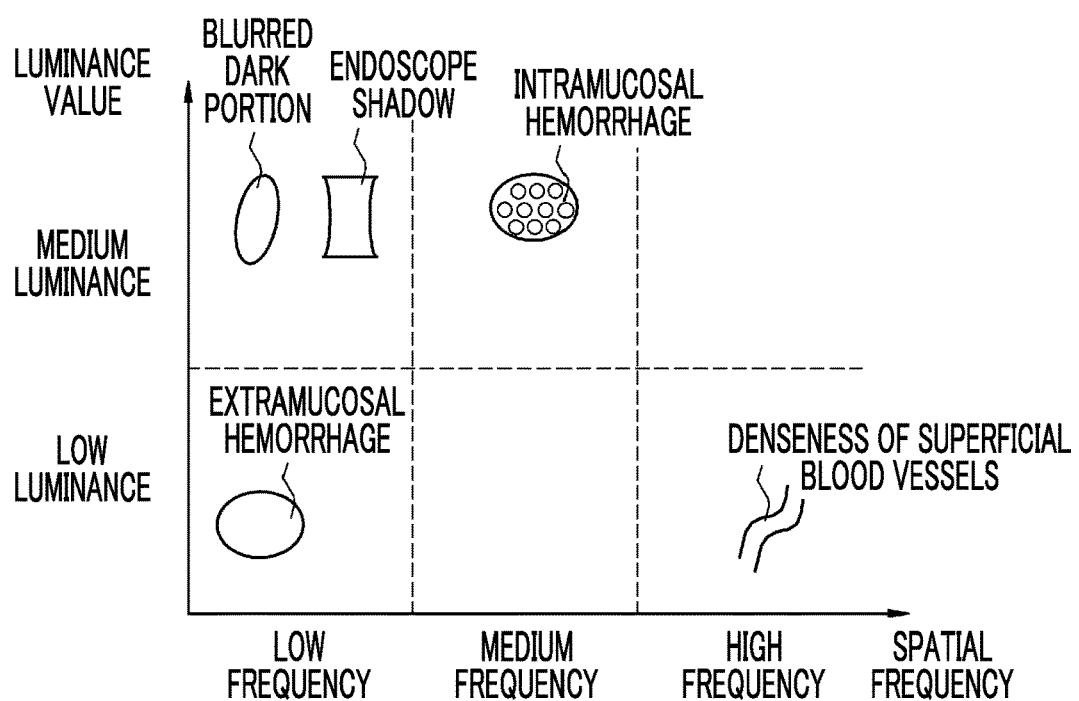
FIG. 8 is a diagram showing the denseness of superficial blood vessels, intramucosal hemorrhage, and extramucosal hemorrhage that are classified depending on a luminance value and a spatial frequency.

The disease-related processing section 66 classifies the denseness of superficial blood vessels, intramucosal hemorrhage, and extramucosal hemorrhage depending on a frequency characteristic or a luminance value obtained from the special image, and determines whether or not ulcerative colitis has remitted according to the classification. Specifically, the denseness of superficial blood vessels, intramucosal hemorrhage, and extramucosal hemorrhage are classified as shown in FIG. 8. The denseness of superficial blood vessels is represented by a low luminance value and a high frequency characteristic. Intramucosal hemorrhage is represented by a medium luminance value and a medium frequency characteristic. Extramucosal hemorrhage is represented by a low luminance value and a low frequency characteristic. In a case where various structures of the special image are represented by luminance values and frequency characteristics, a blurred dark portion or an endoscope shadow (a shadow that can be formed at the central portion of an endoscopic image in a case where the distal end part 12d of the endoscope is moved along the lumen) of the special image and the like are also included in addition to the above-mentioned three, that is, the denseness of superficial blood vessels, intramucosal hemorrhage, and extramucosal hemorrhage. In this embodiment, the denseness of superficial blood vessels, intramucosal hemorrhage, and extramucosal hemorrhage, which are required to determine whether or not ulcerative colitis has remitted, are extracted from the special image using the above-mentioned classification.

Figure 9:
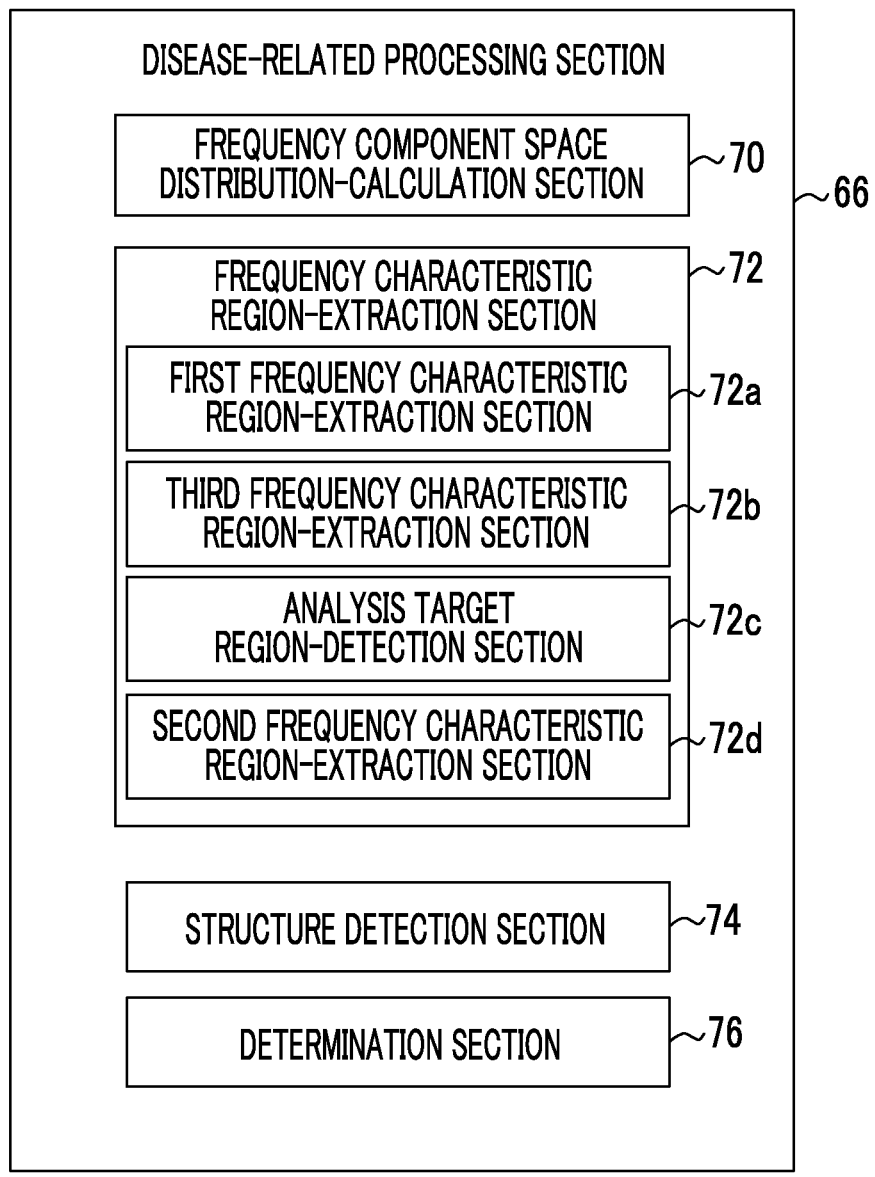
FIG. 9 is a block diagram showing the functions of a disease-related processing section.

As shown in FIG. 9, the disease-related processing section 66 comprises a frequency component space distribution-calculation section 70, a frequency characteristic region-extraction section 72, a structure detection section 74, and a determination section 76. The frequency component space distribution-calculation section 70 calculates a frequency component-space distribution by applying Laplacian filter to the special image.

On the basis of the frequency component-space distribution, the frequency characteristic region-extraction section 72 extracts a first frequency characteristic region (low frequency region) having a first frequency characteristic (low frequency), extracts a second frequency characteristic region (medium frequency region) having a second frequency characteristic (medium frequency) having a frequency higher than the frequency of the first frequency characteristic, and extracts a third frequency characteristic region (high frequency region) having a third frequency characteristic (high frequency) having a frequency higher than the frequency of the second frequency characteristic.

Figure 10:
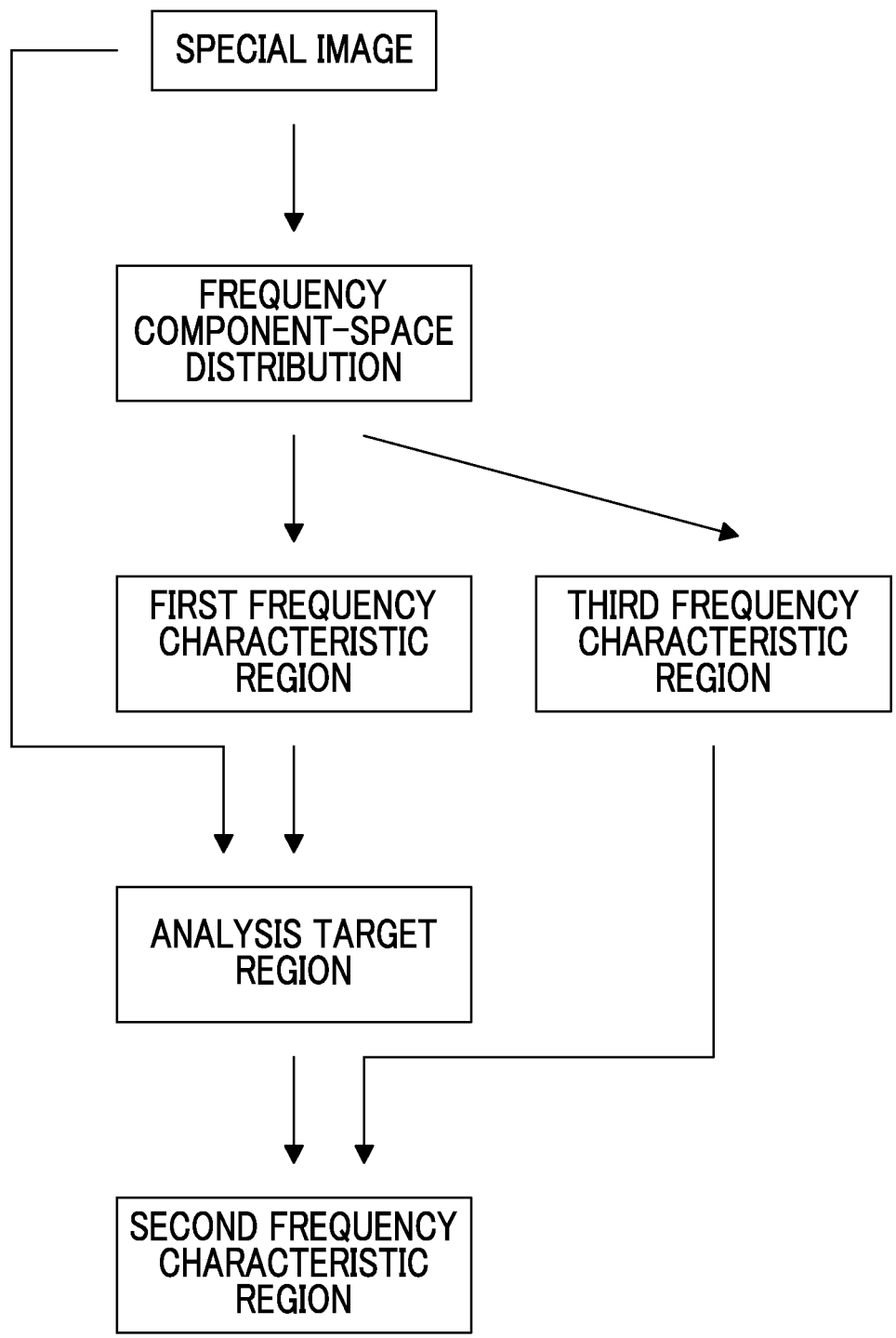
FIG. 10 is a diagram showing a series of flows for extracting a first frequency characteristic region, a second frequency characteristic region, and a third frequency characteristic region.

Specifically, the frequency characteristic region-extraction section 72 comprises a first frequency characteristic region-extraction section 72a, a third frequency characteristic region-extraction section 72b, a analysis target region-detection section 72c, and a second frequency characteristic region-extraction section 72d; and extracts the first to third frequency characteristic regions according to a flow shown in FIG. 10. In a case where the standard deviation of the frequencies of nine pixels, which are disposed near a region including a specific pixel, is equal to or smaller than a constant value, the first frequency characteristic region-extraction section 72a determines that the specific pixel is a pixel belonging to the first frequency characteristic on the basis of the frequency component-space distribution. The first frequency characteristic region-extraction section 72a extracts the first frequency characteristic region by performing the detection of the specific pixel for all the pixels. The first frequency characteristic region corresponds to a low frequency region. The third frequency characteristic region-extraction section 72b extracts the third frequency characteristic region by Hessian analysis for the frequency component-space distribution. The third frequency characteristic region corresponds to a high frequency region. In a case where the standard deviation of the frequencies of nine pixels, which are disposed near a region including a specific pixel, is equal to or smaller than a constant value, the first frequency characteristic region-extraction section 72a determines that the specific pixel is a pixel belonging to the first frequency characteristic. However, in a case where another statistic, for example, the maximum value, the minimum value, or the average value of the frequencies of nine pixels, which are disposed near the region, is equal to or smaller than a constant value, the first frequency characteristic region-extraction section 72a may determine that the specific pixel is a pixel belonging to the first frequency characteristic.

The analysis target region-detection section 72c detects an analysis target region that excludes the first frequency characteristic region from the special image. The second frequency characteristic region-extraction section 72d extracts the second frequency characteristic region by excluding the third frequency characteristic region from the analysis target region. The second frequency characteristic region corresponds to a medium frequency region.

The structure detection section 74 detects the denseness of superficial blood vessels, intramucosal hemorrhage, and extramucosal hemorrhage on the basis of the first frequency characteristic region that is subjected to first region determination processing using a luminance value, the second frequency characteristic region that is subjected to second region determination processing using a luminance value, and the third frequency characteristic region. Specifically, the structure detection section 74 detects extramucosal hemorrhage by performing the first region determination processing on the first frequency characteristic region, detects intramucosal hemorrhage by performing the second region determination processing on the second frequency characteristic region, and detects the third frequency characteristic region as the denseness of superficial blood vessels.

Since the first frequency characteristic region having a low frequency includes a blurred dark portion or an endoscope shadow having medium luminance in addition to extramucosal hemorrhage having low luminance, the first region determination processing is performed to distinguish these. In the first region determination processing, a region, of which the luminance value is equal to or smaller than a threshold value for a luminance value, of the first frequency characteristic region of the special image is detected as a region of extramucosal hemorrhage. The second region determination processing is performed to distinguish intramucosal hemorrhage having medium luminance. In the second region determination processing, a region, of which the luminance value is equal to or larger than a threshold value for a luminance value, of the second frequency characteristic region of the special image is detected as a region of intramucosal hemorrhage. Third region determination processing may be performed to distinguish the denseness of superficial blood vessels having low luminance. In the third region determination processing, a region, of which the luminance value is equal to or smaller than a threshold value for a luminance value, of the third frequency characteristic region of the special image is detected as a region where superficial blood vessels are dense.

Figure 11:
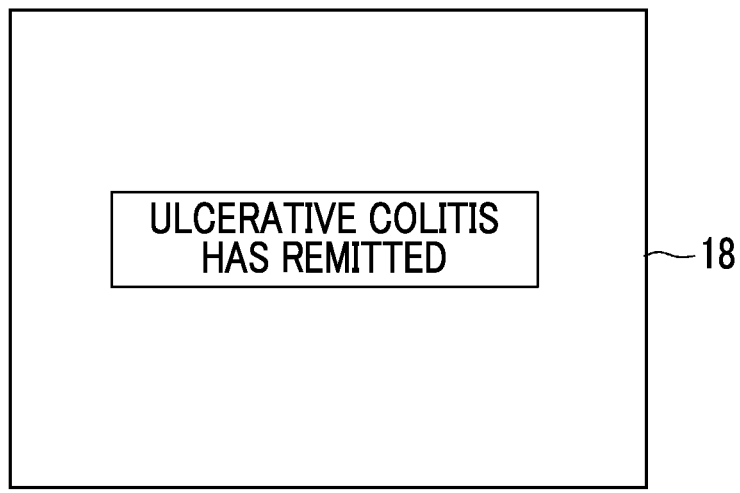
FIG. 11 is an image diagram of a monitor that displays information related to determination.

In a case where any of a condition where superficial blood vessels are dense, a condition where the amount of the detected intramucosal hemorrhage is equal to or larger than a threshold value for intramucosal hemorrhage, a condition where the amount of the detected extramucosal hemorrhage is equal to or larger than a threshold value for extramucosal hemorrhage, or a condition where the sum of the amount of the detected intramucosal hemorrhage and the amount of the detected extramucosal hemorrhage is equal to or larger than a threshold value for intramucosal/extramucosal hemorrhage is satisfied, the determination section 76 determines that ulcerative colitis has not remitted. On the other hand, in a case where all of the condition where superficial blood vessels are dense, the condition where the amount of the detected intramucosal hemorrhage is equal to or larger than the threshold value for intramucosal hemorrhage, the condition where the amount of the detected extramucosal hemorrhage is equal to or larger than the threshold value for extramucosal hemorrhage, and the condition where the sum of the amount of the detected intramucosal hemorrhage and the amount of the detected extramucosal hemorrhage is the threshold value for intramucosal/extramucosal hemorrhage are not satisfied, the determination section 76 determines that ulcerative colitis has remitted. Information about the determination of the above-mentioned determination section 76 is displayed on the monitor 18, and is used in a case where a user determines whether or not ulcerative colitis has remitted. In a case where the determination section 76 determines that ulcerative colitis has remitted, a message that ulcerative colitis has remitted is displayed on the monitor 18 as shown in FIG. 11. It is preferable that the special image used for the determination of the determination section 76 is superimposed and displayed in a case where the information about the determination is displayed.

It is preferable that the amount of the detected intramucosal hemorrhage is calculated in the determination section 76 on the basis of a ratio of a region of the special image occupied by the second frequency characteristic region. Further, it is preferable that the amount of the detected extramucosal hemorrhage is calculated in the determination section 76 on the basis of a ratio of a region of the special image occupied by the first frequency characteristic region having low luminance (the first frequency characteristic region having been subjected to the first region determination processing). Furthermore, in addition to or instead of the determination of whether or not ulcerative colitis has remitted, the determination section 76 may obtain an index value indexing the severity of ulcerative colitis, determine whether or not ulcerative colitis has remitted according to the index value, and display the index value on the monitor 18 as a determination result.

Figure 12:
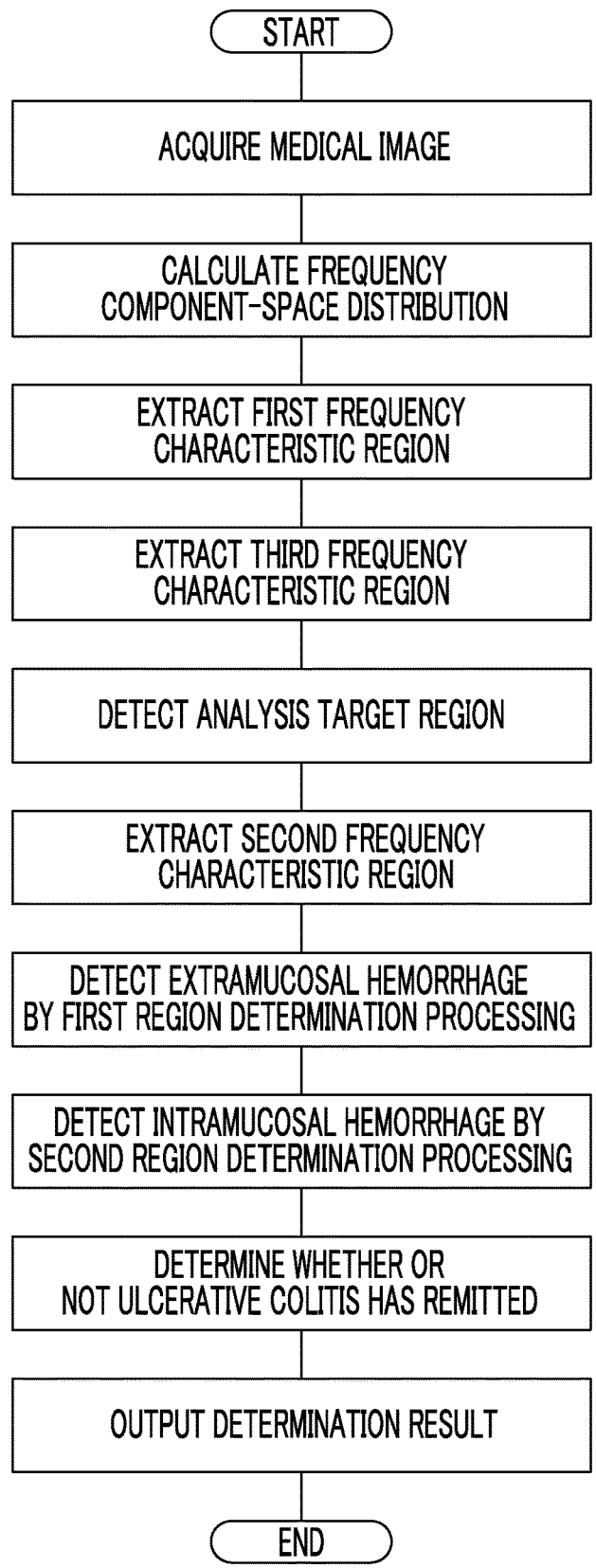
FIG. 12 is a flowchart showing a series of flows of a disease-related processing mode.

Next, a series of flows of the disease-related processing mode will be described with reference to a flowchart shown in FIG. 12. In a case where a mode is switched to the disease-related processing mode, the object to be observed is irradiated with special light. The endoscope 12 obtains a special image, which is one of endoscopic images (medical images), by picking up the image of the object to be observed illuminated with special light. The image acquisition unit 50 acquires the special image that is obtained from the endoscope 12.

The frequency component space distribution-calculation section 70 calculates a frequency component-space distribution from the special image. The first frequency characteristic region-extraction section 72a extracts a first frequency characteristic region having a low frequency on the basis of the frequency component-space distribution. Further, the third frequency characteristic region-extraction section 72b extracts a third frequency characteristic region having a high frequency on the basis of the frequency component-space distribution. The analysis target region-detection section 72c detects an analysis target region that excludes the first frequency characteristic region from the medical image. The second frequency characteristic region-extraction section 72d extracts a second frequency characteristic region having a medium frequency by excluding the third frequency characteristic region from the analysis target region.

The structure detection section 74 detects extramucosal hemorrhage by performing the first region determination processing on the first frequency characteristic region having a low frequency. Furthermore, the structure detection section 74 detects intramucosal hemorrhage by performing the second region determination processing on the second frequency characteristic region having a medium frequency. Moreover, the structure detection section 74 detects the third frequency characteristic region as the denseness of superficial blood vessels.

The determination section 76 determines whether or not ulcerative colitis has remitted on the basis of the denseness of superficial blood vessels, intramucosal hemorrhage, and extramucosal hemorrhage that are detected by the structure detection section 74. Information about the determination of the determination section 76 is displayed on the monitor 18.

Second Embodiment

In a second embodiment, an object to be observed is illuminated using a broadband light source, such as a xenon lamp, and a rotary filter instead of the four color LEDs 20a to 20d described in the first embodiment. Further, the image of the object to be observed is picked up by a monochrome image pickup sensor instead of the color image pickup sensor 44. Others are the same as those of the first embodiment.

Figure 13:
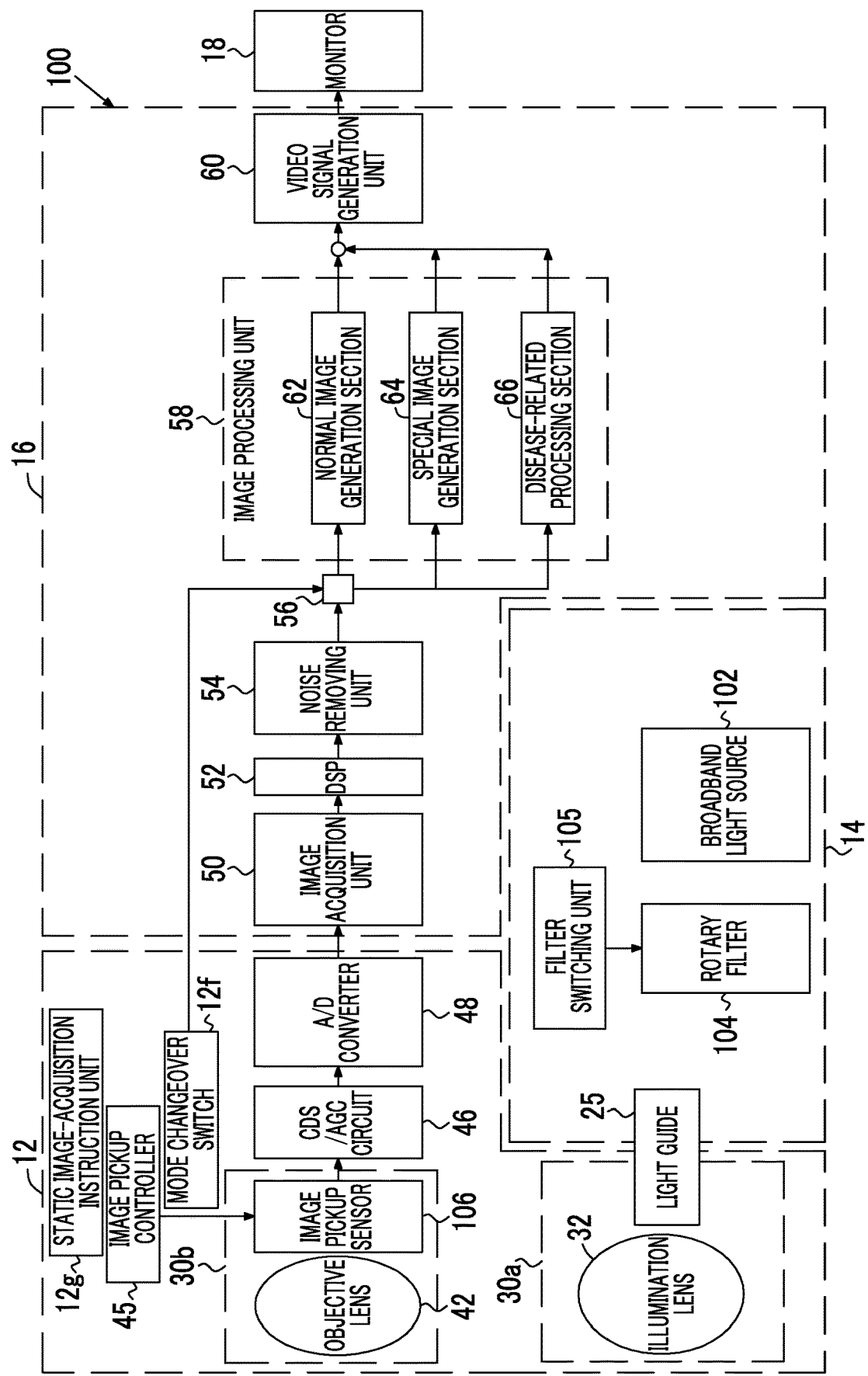
FIG. 13 is a block diagram showing the functions of an endoscope system of a second embodiment.

As shown in FIG. 13, in an endoscope system 100 of the second embodiment, a light source device 14 is provided with a broadband light source 102, a rotary filter 104, and a filter switching unit 105 instead of the four color LEDs 20a to 20d. Further, an image pickup optical system 30b is provided with a monochrome image pickup sensor 106, which is not provided with color filters, instead of the color image pickup sensor 44.

The broadband light source 102 is a xenon lamp, a white LED, or the like, and emits white light of which the wavelength range reaches the wavelength range of red light from the wavelength range of blue light. The rotary filter 104 is provided with a filter 107 for a normal light mode and a filter 108 for a special light mode and a disease-related processing mode that are arranged in this order from the inside (see FIG. 14). The filter switching unit 105 is to move the rotary filter 104 in a radial direction, inserts the filter 107 for a normal light mode into the optical path of white light in a case where the endoscope system 100 is set to a normal light mode by a mode changeover SW 12f, and inserts the filter 108 for a special light mode and a disease-related processing mode into the optical path of white light in a case where the endoscope system 100 is set to a special light mode or a disease-related processing mode.

Figure 14:
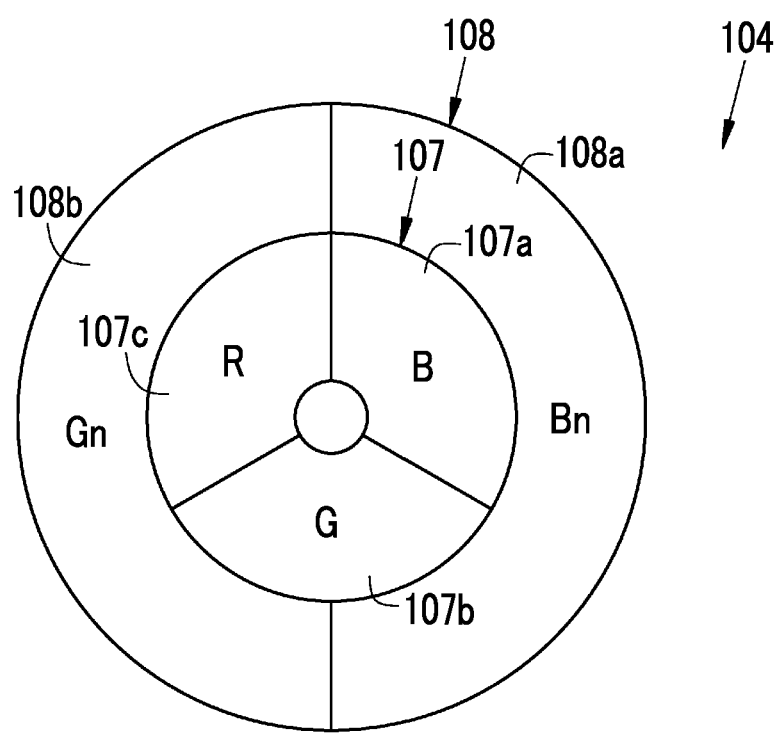
FIG. 14 is a plan view of a rotary filter.

As shown in FIG. 14, the filter 107 for a normal light mode is provided with a B-filter 107a, a G-filter 107b, and an R-filter 107c that are arranged in a circumferential direction. The B-filter 107a transmits broadband blue light B of white light, the G-filter 107b transmits broadband green light G of white light, and the R-filter 107c transmits broadband red light R of white light. Accordingly, in the normal light mode, the rotary filter 104 is rotated to allow the object to be observed to be alternately irradiated with broadband blue light B, broadband green light G, and broadband red light R as normal light.

The filter 108 for a special light mode and a disease-related processing mode is provided with a Bn-filter 108a and a Gn-filter 108b that are arranged in the circumferential direction. The Bn-filter 108a transmits narrow-band blue light of white light, and the Gn-filter 108b transmits narrow-band green light of white light. Accordingly, in the special light mode or the disease-related processing mode, the rotary filter 104 is rotated to allow the object to be observed to be alternately irradiated with narrow-band blue light and narrow-band green light, which are short-wavelength light, as special light. It is preferable that the wavelength range of the narrow-band blue light is in the range of 400 to 450 nm and the wavelength range of the narrow-band green light is in the range of 540 to 560 nm.

In the endoscope system 100, the image of the object to be observed is picked up by the monochrome image pickup sensor 106 whenever the object to be observed is illuminated with broadband blue light B, broadband green light G, and broadband red light R in the normal light mode. Accordingly, Bc-image signals, Gc-image signals, and Rc-image signals are obtained. Then, a normal image is generated on the basis of these three colors image signals by the same method as the first embodiment.

In the endoscope system 100, the image of the object to be observed is picked up by the monochrome image pickup sensor 106 whenever the object to be observed is illuminated with narrow-band blue light and narrow-band green light in the special light mode or the disease-related processing mode. Accordingly, Bs-image signals and Gs-image signals are obtained. Then, a special image is generated on the basis of these two colors image signals by the same method as the first embodiment.

Third Embodiment

In a third embodiment, an object to be observed is illuminated using a laser light source and a phosphor instead of the four color LEDs 20a to 20d described in the first embodiment. Only portions different from those of the first embodiment will be described below and the description of substantially the same portions as those of the first embodiment will be omitted.

Figure 15:
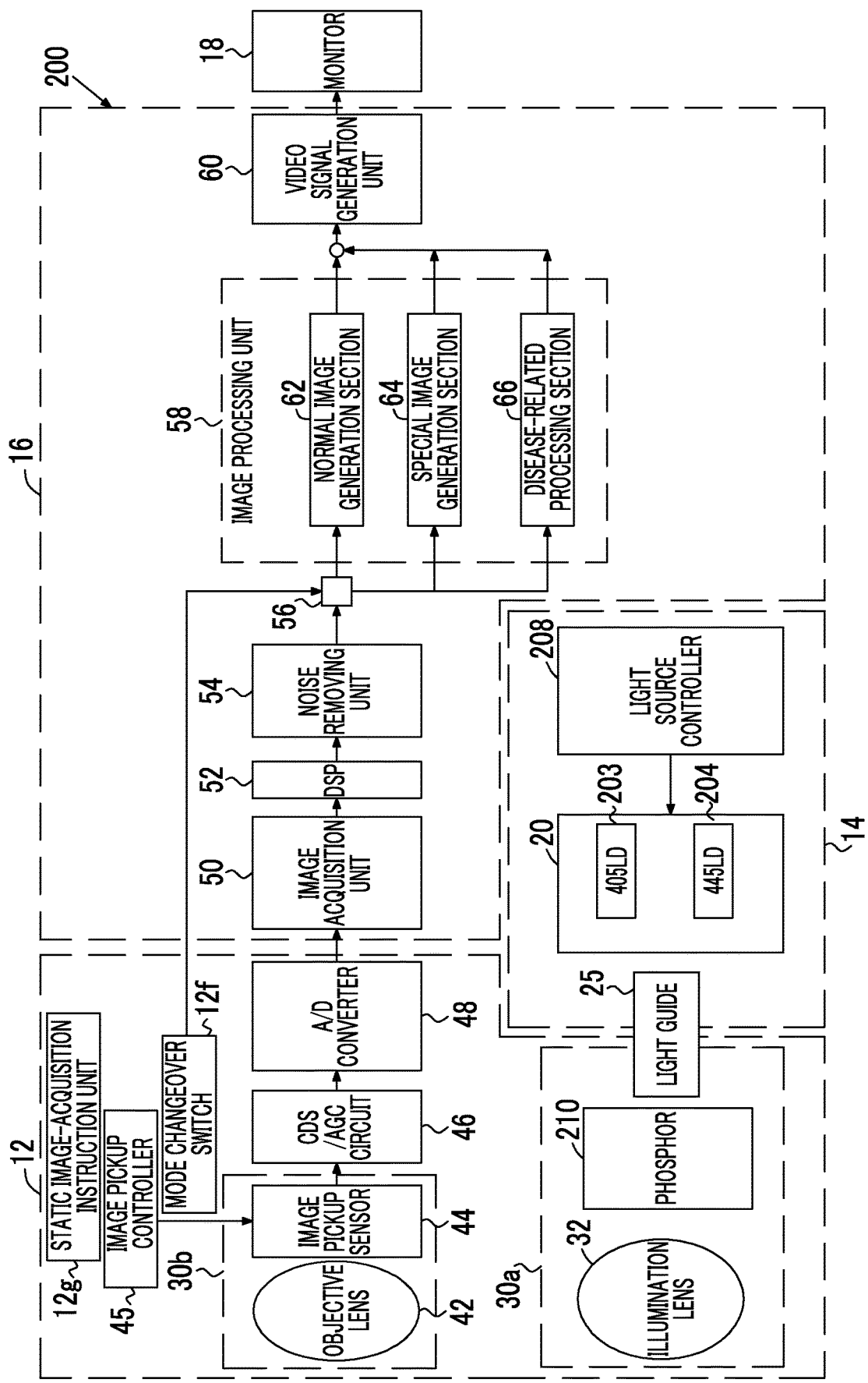
FIG. 15 is a block diagram showing the functions of an endoscope system of a third embodiment.

As shown in FIG. 15, in an endoscope system 200 of the third embodiment, a light source unit 20 of a light source device 14 is provided with a violet laser light source unit (written as "405LD". LD represents "Laser Diode") 203 that emits violet laser light which corresponds to short-wavelength light and of which the central wavelength is in the range of 405±10 nm and a blue laser light source unit (written as "445LD") 204 that emits blue laser light of which the central wavelength is in the range of 445±10 nm, instead of the four color LEDs 20a to 20d. The emission of light from semiconductor light-emitting elements of these respective light source units 203 and 204 is individually controlled by a light source controller 208.

The light source controller 208 turns on the blue laser light source unit 204 in a normal light mode. In contrast, the light source controller 208 simultaneously turns on the violet laser light source unit 203 and the blue laser light source unit 204 in a special light mode or a disease-related processing mode.

It is preferable that the half-width of violet laser light or blue laser light is set to about ±10 nm. Further, broad area-type InGaN-based laser diodes can be used as the violet laser light source unit 203 and the blue laser light source unit 204, and InGaNAs-based laser diodes or GaNAs-based laser diodes can also be used. Furthermore, a light emitter, such as a light emitting diode, may be used as the light source.

An illumination optical system 30a is provided with a phosphor 210, on which blue laser light emitted from the light guide 25 is incident, in addition to an illumination lens 32. The phosphor 210 is excited by blue laser light and emits fluorescence. Accordingly, blue laser light corresponds to excitation light. Further, a part of blue laser light is transmitted without exciting the phosphor 210. The inside of the object to be observed is illuminated with light, which is emitted from the phosphor 210, through the illumination lens 32.

Figure 16:
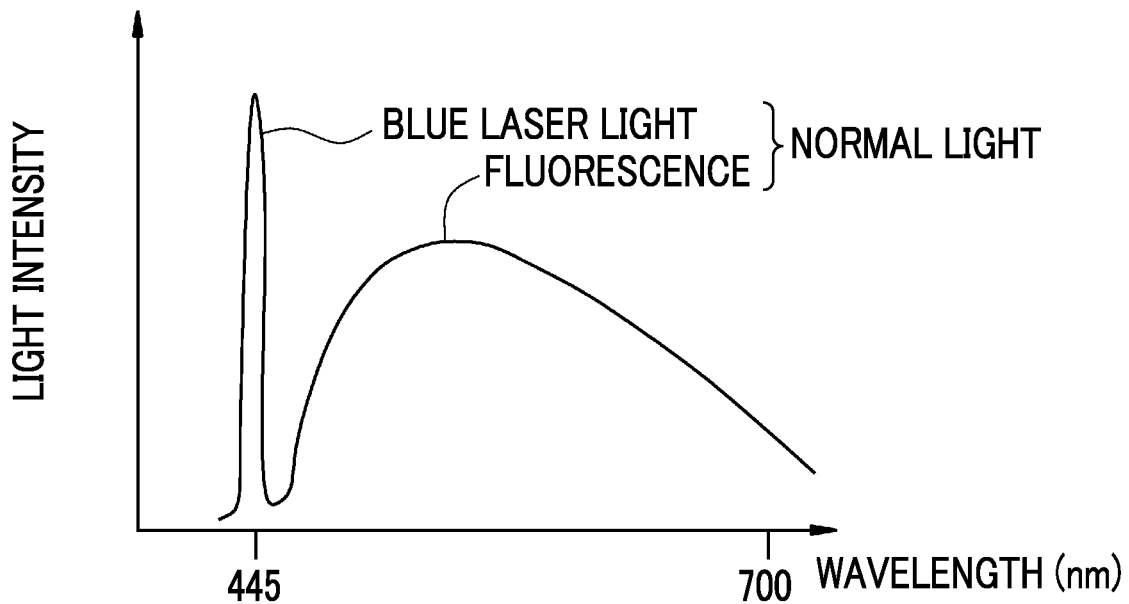
FIG. 16 is a graph showing the spectrum of normal light of the third embodiment.

Here, since blue laser light is mainly incident on the phosphor 210 in the normal light mode, the object to be observed is illuminated with normal light in which blue laser light and fluorescence, which is excited and emitted from the phosphor 210 by blue laser light, are multiplexed as shown in FIG. 16. The image of the object to be observed illuminated with this normal light is picked up by an image pickup sensor 44, so that a normal image consisting of Bc-image signals, Gc-image signals, and Rc-image signals is obtained.

Figure 17:
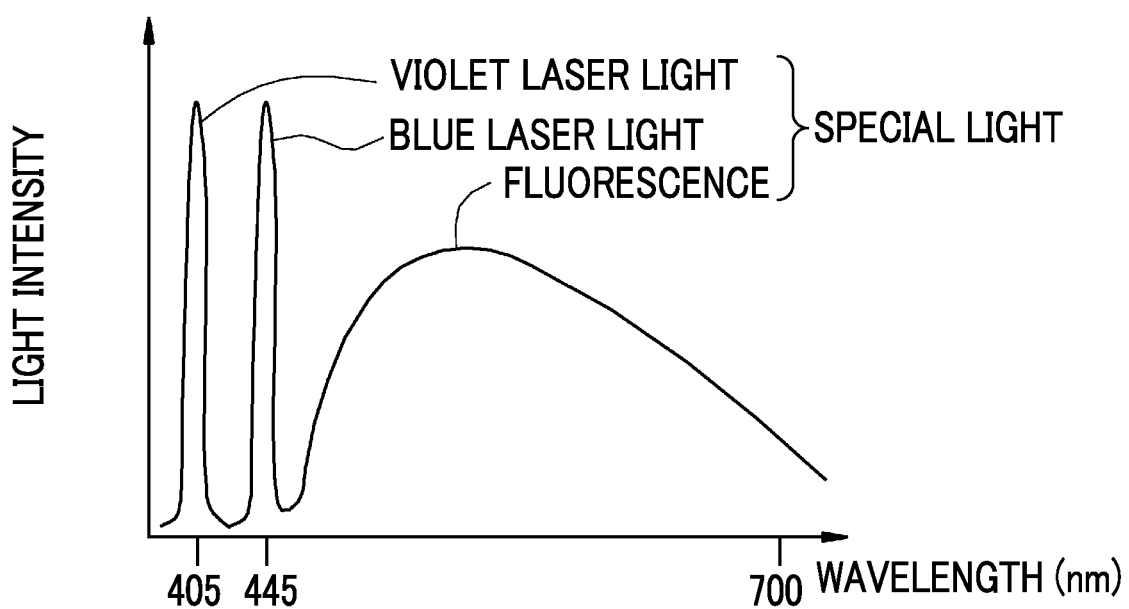
FIG. 17 is a graph showing the spectrum of special light of the third embodiment.

Further, violet laser light and blue laser light are simultaneously incident on the phosphor 210 in the special light mode or the disease-related processing mode, so that pseudo-white light, which includes fluorescence excited and emitted from the phosphor 210 by violet laser light and blue laser light in addition to violet laser light and blue laser light, is emitted as special light as shown in FIG. 17. The image of the object to be observed illuminated with this special light is picked up by the image pickup sensor 44, so that a special image consisting of Bs-image signals, Gs-image signals, and Rs-image signals is obtained. Pseudo-white light may be light in which violet light V, blue light B, green light G, and red light emitted from the V-LED 20a, the B-LED 20b, the G-LED 20c, and the R-LED 20d are combined.

It is preferable that a phosphor including a plurality of types of phosphor absorbing a part of blue laser light and exciting and emitting green to yellow light (for example, YKG-based phosphors or phosphors, such as BAM ($BaMgAl_{10}O_{17}$)) is used as the phosphor 210. In a case where the semiconductor light-emitting elements are used as the excitation light source of the phosphor 210 as in this configuration example, high-intensity white light is obtained with high luminous efficiency. Accordingly, not only the intensity of white light can be easily adjusted but also a change in the color temperature and chromaticity of white light can be suppressed to be small.

The invention has been applied to the endoscope system for processing an endoscopic image, which is one of medical images, in the embodiments, but the invention can also be applied to medical image processing systems for processing medical images other than an endoscopic image. Further, the invention can also be applied to a diagnosis support device for providing diagnostic support to a user using a medical image. Furthermore, the invention can also be applied to a medical service support device for supporting a medical service, such as a diagnostic report, using a medical image.

Figure 18:
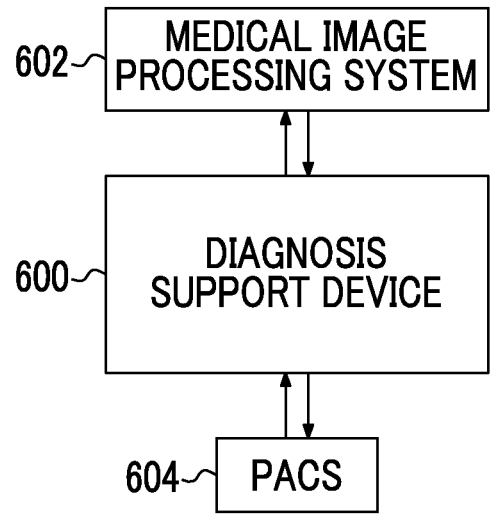
FIG. 18 is a block diagram showing a diagnosis support device.
Figure 19:
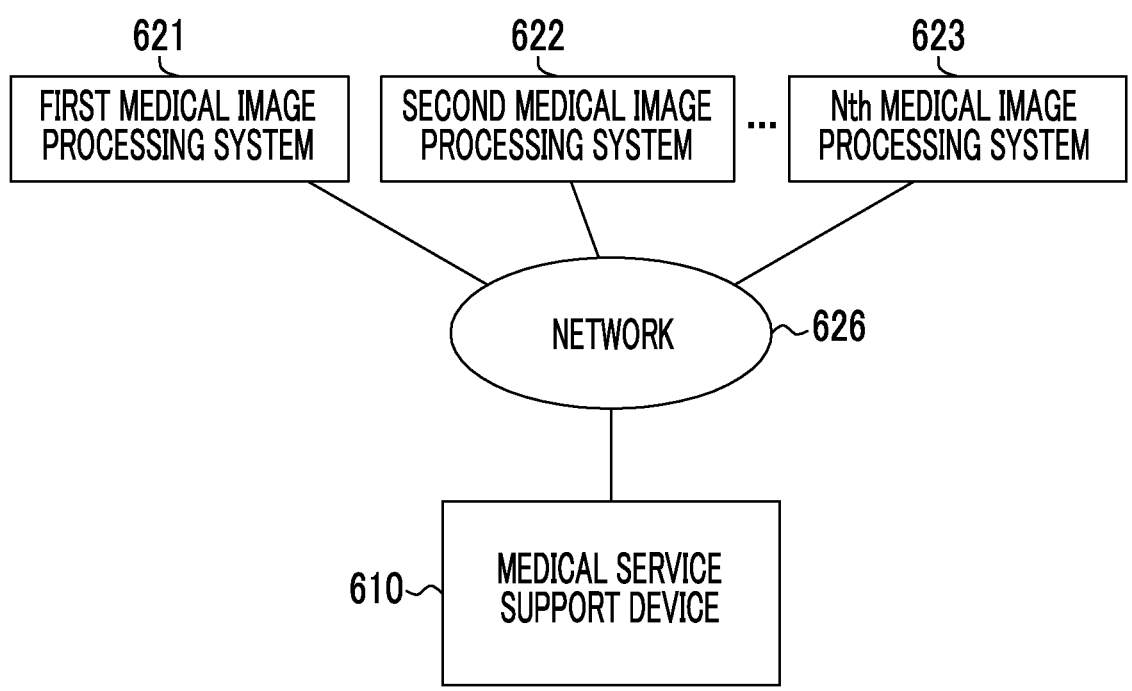
FIG. 19 is a block diagram showing a medical service support device.

For example, as shown in FIG. 18, a diagnosis support device 600 is used in combination with the modality of a medical image processing system 602 or the like and a picture archiving and communication system (PACS) 604. Further, as shown in FIG. 19, a medical service support device 610 is connected to various inspection apparatuses, such as a first medical image processing system 621, a second medical image processing system 622, . . . , and an Nth medical image processing system 623, through an arbitrary network 626. The medical service support device 610 receives medical images from the first to Nth medical image processing systems 621, 622, . . . , and 623, and supports a medical service on the basis of the received medical images.

The hardware structures of processing units for performing various types of processing, such as the normal image generation section 62, the special image generation section 64, the disease-related processing section 66, the frequency component space distribution-calculation section 70, the frequency characteristic region-extraction section 72, the first frequency characteristic region-extraction section 72a, the third frequency characteristic region-extraction section 72b, the analysis target region-detection section 72c, the second frequency characteristic region-extraction section 72d, the structure detection section 74, and the determination section 76 included in the image processing unit 58 in the above-mentioned embodiments, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a dedicated electrical circuit that is a processor having circuit configuration designed exclusively to perform various types of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed of one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope system
12: endoscope
12a: insertion part
12b: operation part
12c: bendable part
12d: distal end part
12e: angle knob
12f: mode changeover switch
12g: static image-acquisition instruction unit
14: light source device
16: processor device
18: monitor
19: console
20: light source unit
20a: V-LED
20b: B-LED
20c: G-LED
20d: R-LED
21: light source controller
23: optical path-combination unit
25: light guide
30a: illumination optical system
30b: image pickup optical system
32: illumination lens
42: objective lens
44: image pickup sensor
45: image pickup controller
46: CDS/AGC circuit
48: A/D converter
50: image acquisition unit
52: DSP
54: noise removing unit
56: image processing switching unit
58: image processing unit
60: video signal generation unit
62: normal image generation section
64: special image generation section
66: disease-related processing section
70: frequency component space distribution-calculation section
72: frequency characteristic region-extraction section
72a: first frequency characteristic region-extraction section
72b: third frequency characteristic region-extraction section
72c: analysis target region-detection section
72d: second frequency characteristic region-extraction section
74: structure detection section
76: determination section
100: endoscope system
102: broadband light source
104: rotary filter
105: filter switching unit
106: image pickup sensor
107: filter for a normal light mode
107a: B-filter
107b: G-filter
107c: R-filter
108: filter for a special light mode and a disease-related processing mode
108a: Bn-filter
108b: Gn-filter
200: endoscope system
203: violet laser light source unit
204: blue laser light source unit
208: light source controller
210: phosphor
600: diagnosis support device
602: medical image processing system
604: PACS
610: medical service support device
621: first medical image processing system
622: second medical image processing system
623: Nth medical image processing system
626: network

What is claimed is:

1. An image processing device comprising:
a processor configured to:
acquire a medical image obtained from image pickup of an object to be observed; and
perform at least one of calculation of an index value related to a stage of ulcerative colitis, determination of the stage of the ulcerative colitis, or determination of whether or not the ulcerative colitis has remitted, on the basis of denseness of superficial blood vessels, intramucosal hemorrhage, and extramucosal hemorrhage obtained from the medical image;
calculate a frequency component-space distribution from the medical image;
extract a first frequency characteristic region having a first frequency characteristic;
extract a second frequency characteristic region having a second frequency characteristic having a frequency higher than a frequency of the first frequency characteristic;
extract a third frequency characteristic region having a third frequency characteristic having a frequency higher than the frequency of the second frequency characteristic on the basis of the frequency component-space distribution;
detect the denseness of the superficial blood vessels, the intramucosal hemorrhage, and the extramucosal hemorrhage on the basis of the first frequency characteristic region, the second frequency characteristic region, and the third frequency characteristic region; and
determine whether or not the ulcerative colitis has remitted on the basis of the detected denseness of the superficial blood vessels, the detected intramucosal hemorrhage, and the detected extramucosal hemorrhage.

2. The image processing device according to claim 1, wherein the processor further configured to:
classify the denseness of the superficial blood vessels, the intramucosal hemorrhage, and the extramucosal hemorrhage depending on a frequency characteristic or a luminance value obtained from the medical image; and
determine whether or not the ulcerative colitis has remitted according to the classification.

3. The image processing device according to claim 1, wherein the processor is further configured to:
detect an analysis target region that excludes the first frequency characteristic region from the medical image; and extract the second frequency characteristic region by excluding the third frequency characteristic region from the analysis target region.

4. The image processing device according to claim 1, wherein the processor is further configured to:
detect the extramucosal hemorrhage by performing the first region determination processing on the first frequency characteristic region;
detect the intramucosal hemorrhage by performing the second region determination processing on the second frequency characteristic region; and
detect the third frequency characteristic region as the denseness of the superficial blood vessels.

5. The image processing device according to claim 1, wherein the processor is further configured to:
determine that the ulcerative colitis has remitted in a case where all of the condition where the superficial blood vessels are dense, the condition where the amount of the detected intramucosal hemorrhage is equal to or larger than the threshold value for intramucosal hemorrhage, the condition where the amount of the detected extramucosal hemorrhage is equal to or larger than the threshold value for extramucosal hemorrhage, and the condition where the sum of the amount of the detected intramucosal hemorrhage and the amount of the detected extramucosal hemorrhage is equal to or larger than the threshold value for intramucosal/extramucosal hemorrhage, are not satisfied.

6. The image processing device according to claim 1, wherein the medical image is obtained from the image pickup of the object to be observed that is illuminated with illumination light including short-wavelength light.

7. The image processing device according to claim 6, wherein the illumination light is violet light of which a central wavelength or a peak wavelength includes 410 nm.

8. The image processing device according to claim 6, wherein the illumination light is narrow-band blue light and narrow-band green light as the short-wavelength light, and
the medical image is obtained from the image pickup of the object to be observed that is alternately illuminated with the narrow-band blue light and the narrow-band green light.

9. The image processing device according to claim 6, wherein the illumination light is pseudo-white light including the short-wavelength light and fluorescence that is obtained in a case where a phosphor is irradiated with excitation light.

10. The image processing device according to claim 6, wherein the illumination light includes violet light as the short-wavelength light and blue light, green light, or red light.

11. A method of operating an image processing device, the method comprising:
acquiring a medical image obtained from image pickup of an object to be observed; and
performing at least one of calculation of an index value related to a stage of ulcerative colitis, determination of the stage of the ulcerative colitis, or determination of whether or not the ulcerative colitis has remitted, on the basis of denseness of superficial blood vessels, intramucosal hemorrhage, and extramucosal hemorrhage obtained from the medical image;
calculating a frequency component-space distribution from the medical image;
extracting a first frequency characteristic region having a first frequency characteristic;
extracting a second frequency characteristic region having a second frequency characteristic having a frequency higher than a frequency of the first frequency characteristic;
extracting a third frequency characteristic region having a third frequency characteristic having a frequency higher than the frequency of the second frequency characteristic on the basis of the frequency component-space distribution;
detecting the denseness of the superficial blood vessels, the intramucosal hemorrhage, and the extramucosal hemorrhage on the basis of the first frequency characteristic region, the second frequency characteristic region, and the third frequency characteristic region; and
determining whether or not the ulcerative colitis has remitted on the basis of the detected denseness of the superficial blood vessels, the detected intramucosal hemorrhage, and the detected extramucosal hemorrhage.

* * * * *